US009156912B2

(12) United States Patent
Matsushima et al.

(10) Patent No.: US 9,156,912 B2
(45) Date of Patent: Oct. 13, 2015

(54) IMMUNOLOGICAL RECONSTITUTION PROMOTER OR PROPHYLACTIC AGENT FOR INFECTIONS EACH OF WHICH MAINTAINS GRAFT-VERSUS-TUMOR EFFECT

(75) Inventors: Kouji Matsushima, Tokyo (JP); Satoshi Ueha, Tokyo (JP); Yusuke Shono, Sapporo (JP)

(73) Assignee: The University of Tokyo, Tokyo (JP)

( * ) Notice: Subject to any disclaimer, the term of this patent is extended or adjusted under 35 U.S.C. 154(b) by 144 days.

(21) Appl. No.: 13/139,089

(22) PCT Filed: Nov. 4, 2009

(86) PCT No.: PCT/JP2009/068805
§ 371 (c)(1),
(2), (4) Date: Aug. 17, 2011

(87) PCT Pub. No.: WO2010/067671
PCT Pub. Date: Jun. 17, 2010

(65) Prior Publication Data
US 2012/0027748 A1    Feb. 2, 2012

(30) Foreign Application Priority Data
Dec. 12, 2008   (JP) .................................. 2008-316828

(51) Int. Cl.
| A61K 39/395 | (2006.01) |
| A61K 35/28 | (2015.01) |
| C07K 16/28 | (2006.01) |
| A61K 45/06 | (2006.01) |
| A61K 39/00 | (2006.01) |

(52) U.S. Cl.
CPC ............ *C07K 16/2812* (2013.01); *A61K 39/395* (2013.01); *A61K 45/06* (2013.01); *C07K 16/2815* (2013.01); *A61K 2039/505* (2013.01)

(58) Field of Classification Search
None
See application file for complete search history.

(56) References Cited

U.S. PATENT DOCUMENTS

| 5,178,858 A | 1/1993 | Reichert et al. |
| 5,593,677 A | 1/1997 | Reichert et al. |
| 6,911,220 B1 * | 6/2005 | Sachs ............................ 424/580 |

FOREIGN PATENT DOCUMENTS

| JP | 1-172345 | 7/1989 |
| JP | 2003-246751 | 9/2003 |
| JP | 2003-527096 | 9/2003 |
| WO | WO0045842 | * 4/2000 |
| WO | 01/25405 | 4/2001 |
| WO | WO2004/002425 | * 1/2004 |

OTHER PUBLICATIONS

English translation of the International Preliminary Report on Patentability and Written Opinion dated Jul. 5, 2011.
International Search Report issued Feb. 9, 2010 in International (PCT) Application No. PCT/JP2009/068805.
Certificate of eligibility for exception to lack of novelty of invention including Shono et al., "Suppression of B lymphogenesis in the bone marrow after allogeneic hematopoietic stem cell transplantation: the effect of graft-versus-host reaction" in Proceedings of the Japanese Society for Immunology (JSI), vol. 38, 2008, and its verified English translation.
A. C. Knulst et al., "Prevention of lethal graft-vs.-host disease by a single low dose injection of anti-T cell monoclonal antibody to the allograph recipients", Eur. J. Immunol., vol. 21, No. 1, pp. 103-107, 1991.
K. Ikuta et al., "Ishoku Hentai Shukushubyo (GVHD)", Japanese Journal of Pediatric Medicine, vol. 35, pp. 1297-1302, 2003.

* cited by examiner

*Primary Examiner* — Michail Belyavskyi
(74) *Attorney, Agent, or Firm* — Wenderoth, Lind, Ponack, L.L.P.

(57) ABSTRACT

The object of the invention is to provide an immunological reconstitution promoter or a prophylactic agent for infections for use in allogeneic hematopoietic stem cell transplantation therapy for tumors. The promoter or prophylactic agent enables the amelioration of delayed immune reconstitution or the prevention of infection following transplantation, while maintaining the GVT effect of allogeneic hematopoietic stem cell transplantation. Specifically, in a transplant patient in whom immune reconstitution is delayed, such reconstitution can be promoted by administering, at an early stage following transplantation, a substance capable of depleting CD4$^+$ cells. Early completion of infection management in the patient and improvement in the survival rate are anticipated as a result. In addition, the risk of complications associated with allogeneic hematopoietic stem cell transplantation is reduced, enabling more widespread use of this therapy.

17 Claims, 13 Drawing Sheets

A

Day 14 after HSCT
x200

B

IMMUNOLOGICAL RECONSTITUTION PROMOTER OR PROPHYLACTIC AGENT FOR INFECTIONS EACH OF WHICH MAINTAINS GRAFT-VERSUS-TUMOR EFFECT

This application is a U.S. national stage of International Application No. PCT/JP2009/068805 filed Nov. 4, 2009.

TECHNICAL FIELD

The present invention relates to an immunological reconstitution promoter or a prophylactic agent for infections in allogeneic hematopoietic stem cell transplantation therapy for tumors.

BACKGROUND ART

Hematopoietic stem cell transplantation is a mode of treatment which, after a malignant tumor has been destroyed by a pre-transplant regimen involving a combination of chemotherapy and radiotherapy, builds a new hematopoietic system by the transfusion of donor-derived or the patient's own hematopoietic stem cells. Of these, allogeneic hematopoietic stem cell transplantation involving the transplantation of donor-derived hematopoietic stem cells can be expected to have an anti-tumor effect, i.e., a graft-versus-tumor effect (also referred to below as the "GVT effect"), on various tumors of the hematopoietic system and solid tumors against which other therapeutic methods are likely to be ineffective. However, at the same time, there is a possibility that such therapy may be accompanied by graft-versus-host disease (also referred to below as "GVHD") and by infections attributable to delayed immune reconstitution following transplantation. Such concerns have limited the expansion in the use of this approach as a cancer immunotherapy (Non-Patent Documents 1 and 2).

GVHD is a syndrome characterized by skin rash, jaundice and diarrhea, and is understood to arise from the infiltration of activated donor T-cells into, for example, the skin, liver and intestinal tract. With the appearance of immunosuppressants, which were rapidly developed starting in the late 1980s, the prevention of and treatment outcomes for GVHD improved significantly. At the same time, as a result of the decreased mortality from GVHD, lethal infections associated with immune deficiency following allogeneic hematopoietic stem cell transplantation emerged as a major factor affecting the prognosis of such transplantation. However, the pathogenic mechanism and effective treatments for delayed immune reconstitution following such transplantation have yet to be established. The situation is such that no alternative currently exists but to rely on symptomatic treatment involving the administration of immunoglobulin preparations and antibiotics.

The present invention sets out to employ a substance capable of depleting CD4 positive (also referred to below as CD4$^+$) cells (which substance is also referred to below as a "CD4$^+$ cell-depleting substance") so as to promote immunological reconstitution or prevent infection following allogeneic hematopoietic stem cell transplantation. Such substances have not yet been reported in the literature.

Non-Patent Document 1: Shlomchik, W. D., *Nature Reviews Immunology*, 7(5), 340-352 (2007).
Non-Patent Document 2: Abrahamsen, I. W., and other 5 researchers., *Haematologica*, 90(1), 86-93 (2005).

DISCLOSURE OF THE INVENTION

The object of this invention is to provide an immunological reconstitution promoter or a prophylactic agent for infections in allogeneic hematopoietic stem cell transplantation therapy for tumors.

The inventors, noting that GVHD severity and delayed immune reconstitution exhibit a strong correlation in the clinical course and also that myelosuppression (cytopenia) manifests at the time of GVHD onset, have conducted extensive and repeated investigations. As a result, they have discovered that:

(1) diffuse bleeding, structural breakdown and hematopoietic disorders which arise in bone marrow tissue following allogeneic hematopoietic stem cell transplantation (sometimes referred to below as "bone narrow GVHD") suppress the differentiation and proliferation of T and B lymphocyte precursor cells in the bone narrow, retarding the recovery of cell-mediated immunity and humoral immunity by lymphocytes;
(2) such disorders are caused by donor CD4$^+$ T lymphocytes;
(3) such disorders are ameliorated by treatment involving the depletion of CD4$^+$ T cells at an early stage following such transplantation, promoting T and B lymphocyte reconstitution; and
(4) such treatment does not impair the GVT effect.
Based on these discoveries, the inventors ultimately arrived at the present invention.

Accordingly, the invention provides the following.

[1] A prophylactic agent for infection which maintains a graft-versus-tumor effect of allogeneic hematopoietic stem cell transplantation, comprising a substance capable of depleting CD4 positive cells, and being administered to a tumor patient who has received an allogeneic hematopoietic stem cell transplantation on the same day as transplantation or in the interval from day 1 to about day 60 following transplantation, from once a day to once in about 60 days.

[2] The prophylactic agent for infection of the foregoing [1], which is administered in the interval from day 5 to day 14 following transplantation, from once a day to once in ten days.

[3] The prophylactic agent for infection of the foregoing [1] or [2], wherein the substance capable of depleting CD4 positive cells is a CD4 antibody or an altered and/or modified form thereof.

[4] The prophylactic agent for infection of the foregoing [3], wherein the CD4 antibody is a humanized anti-human CD4 antibody or a human anti-human CD4 antibody.

[5] The prophylactic agent for infection of the foregoing [3], wherein the CD4 antibody is administered in a dose of from 1 to 30 mg/kg each time.

[6] The prophylactic agent for infection of the foregoing [1], wherein the tumor is a hematopoietic tumor.

[7] The prophylactic agent for infection of the foregoing [6], wherein the hematopoietic tumor is acute leukemia, myeloma or malignant lymphoma.

[8] The prophylactic agent for infection of the foregoing [1], wherein the allogeneic hematopoietic stem cell transplantation is bone marrow transplantation, peripheral blood stem cell transplantation or umbilical cord blood transplantation.

[9] The prophylactic agent for infection of the foregoing [1], wherein a donor of the allogeneic hematopoietic stem cell transplantation is a HLA-matched related donor, HLA-matched non-related donor, HLA-mismatched related donor or HLA-mismatched non-related donor.

[10] The prophylactic agent for infection of the foregoing [1], wherein the allogeneic hematopoietic stem cell transplantation is non-myeloablative transplantation or myeloablative transplantation.

[11] The prophylactic agent for infection of the foregoing [1], wherein pre-transplant treatment in allogeneic hematopoietic stem cell transplantation comprises anti-cancer drug administration, exposure to radiation, or a combination thereof.

[12] The prophylactic agent for infection of the foregoing [1], wherein the infection is pathogenic viral infection, pathogenic bacterial infection, pathogenic fungal infection or pathogenic parasitic infection.

[13] The prophylactic agent for Infection of the foregoing [1], wherein the prophylaxis of infection comprises amelioration of delayed immune reconstitution due to a graft-versus-host reaction in bone marrow.

[14] An immunological reconstitution promoter which maintains the graft-versus-tumor effect of allogeneic hematopoietic stem cell transplantation, which comprising a substance capable of depleting CD4 positive cells and being administered to a tumor patient who has received an allogeneic hematopoietic stem cell transplantation on the same day as transplantation or in the interval from day 1 to about day 60 following transplantation, from once a day to once in about 60 days.

The inventive drug makes it possible to promote immunological reconstitution or prevent infections following allogeneic hematopoietic stem cell transplantation, while maintaining the GVT effect of such transplantation.

Specifically, in a tumor patient who has received such a transplantation, especially a patient in whom immune reconstitution is delayed, such reconstitution can be promoted by administering, at an early stage following transplantation, a substance capable of depleting $CD4^+$ cells. Early completion of infection management in the patient and improvement in the survival rate are anticipated as a result. In addition, the risk of complications associated with allogeneic hematopoietic stem cell transplantation is reduced, enabling more widespread use of this therapy.

BRIEF DESCRIPTION OF THE DRAWINGS

(FIGS. 3A, 3B, 3D and 3E are the spleen results, and FIGS. 3C and 3F are the thymus results).

BEST MODE FOR CARRYING OUT THE INVENTION

The invention is described more fully below.

Figure 1:
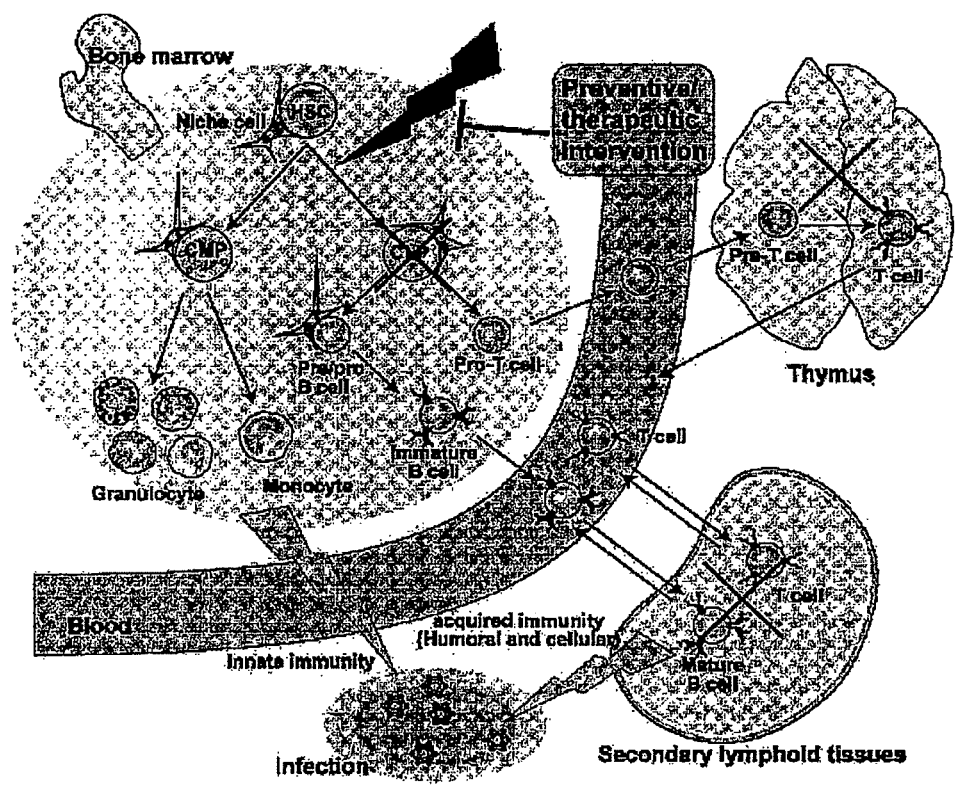
FIG. 1 is a schematic diagram of the pathogenic mechanism for bone marrow GVHD.
Figure 2:
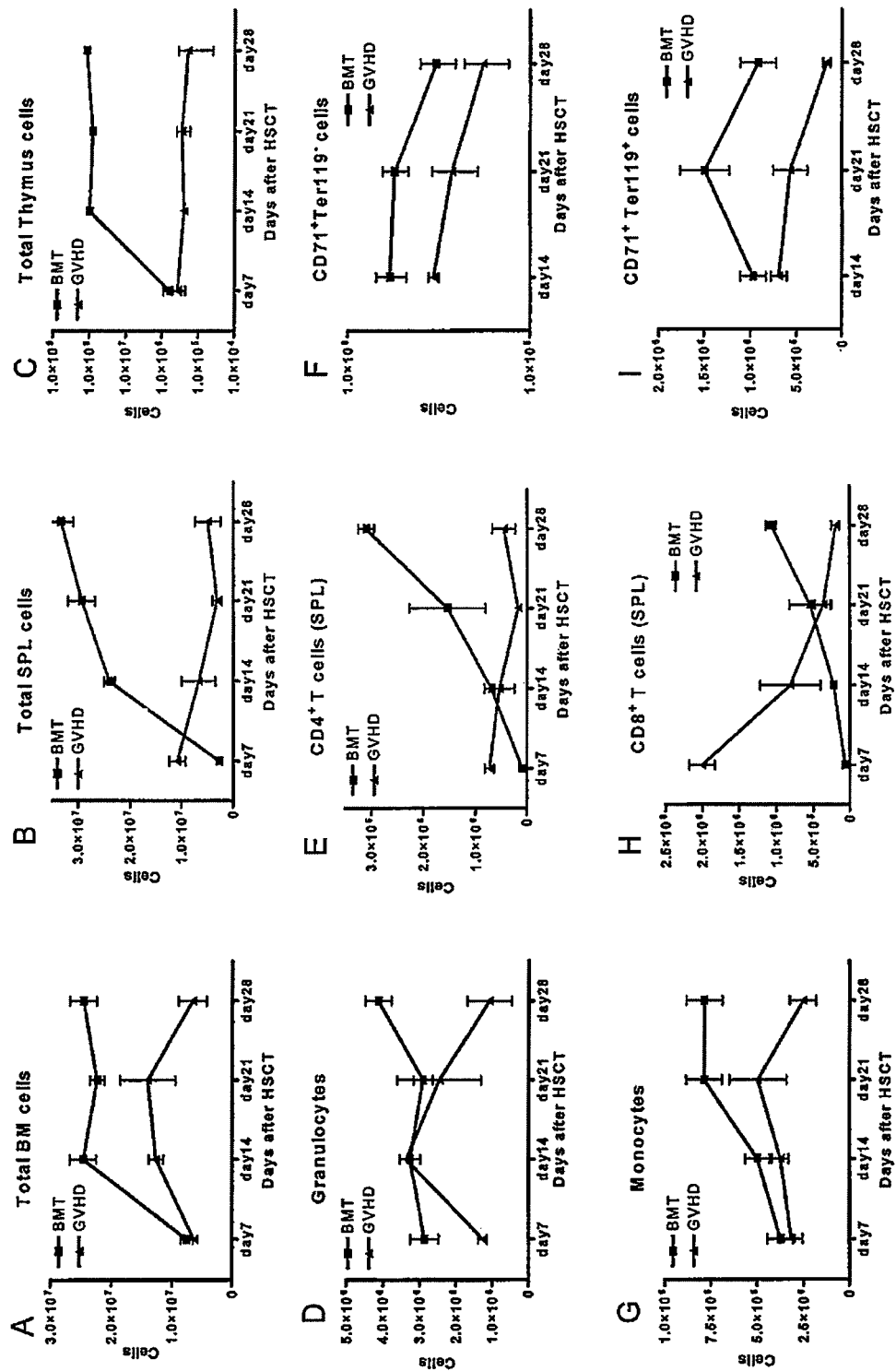
FIG. 2 shows the change over time in the number of each of the following cells in the BMT and GVHD groups: total bone marrow cells (FIG. 2A), total splenic cells (FIG. 2B) and total thymic cells (FIG. 2C); and in the number of each of the following cells in bone marrow within the BMT and GVHD groups: granulocytes (FIG. 2D), monocytes (FIG. 2G), erythroblastic cells ($CD71^+$ and $Ter119^{+/-}$) (FIGS. 2F and 2I), and splenic $CD4^+$ and $CD8^+$ T cells (FIGS. 2E and 2H).
Figure 3:
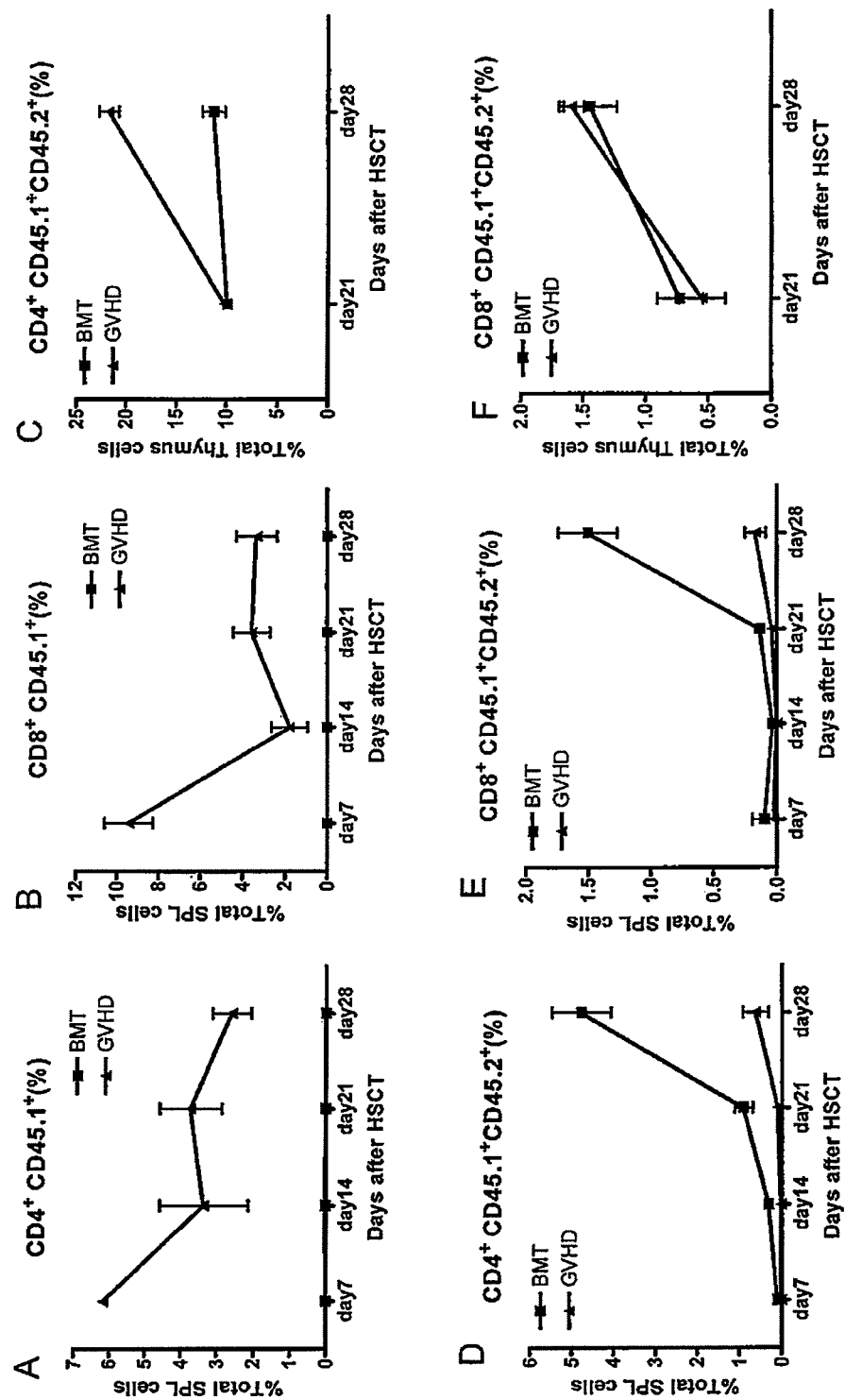
FIG. 3 shows the change over time in the number of each type of donor T cell (FIGS. 3A) and 3B) and donor bone marrow-derived cell (FIGS. 3C to 3F) in the BMT and GVHD groups
Figure 4:
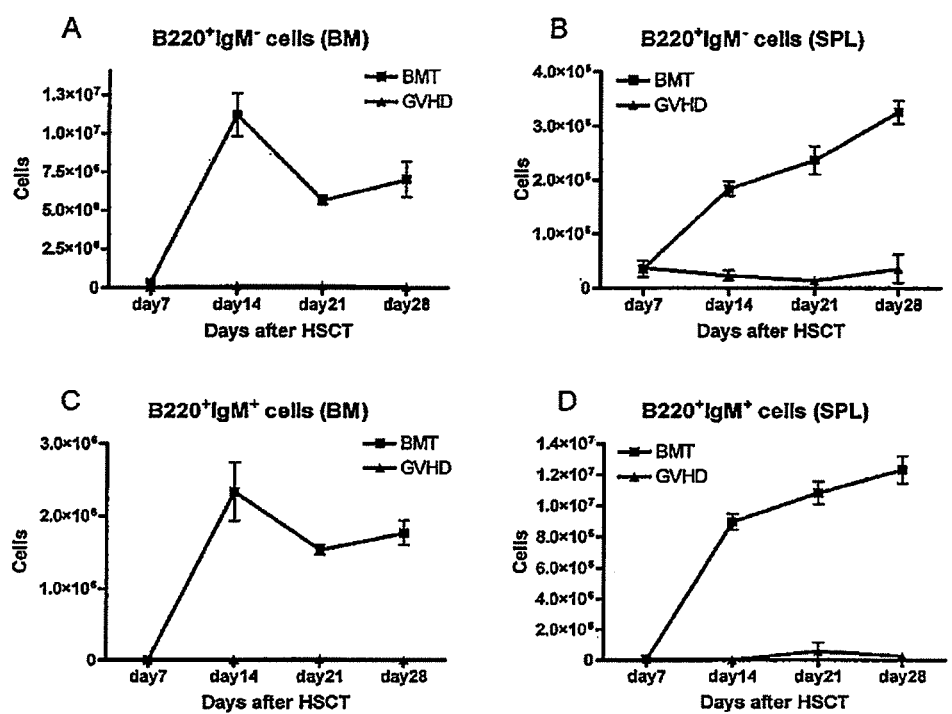
FIG. 4 shows the change over time in the number of B cells in the bone marrow (FIGS. 4A and 4C) and the thymus (FIGS. 4B and 4D) in the BMT and GVHD groups.
Figure 5:
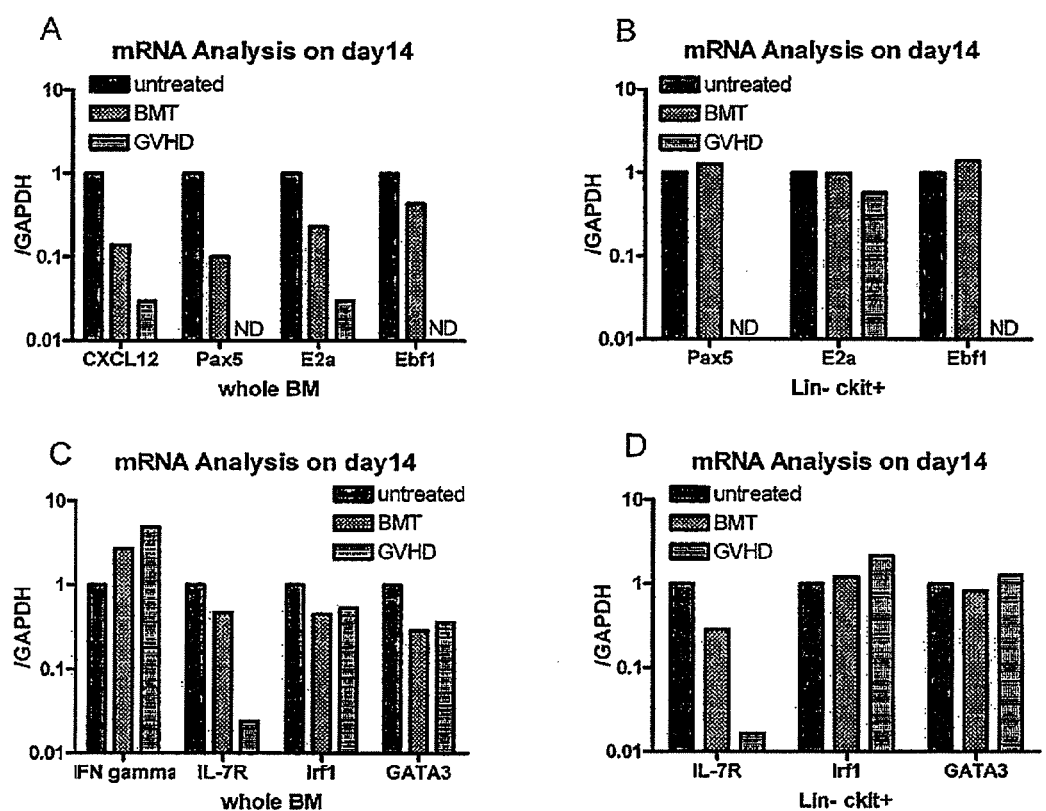
FIG. 5 shows the mRNA expression of factors (CXCL12, Pax5, E2a, Ebf1, IFNgamma, IL-7R, Irf1, GATA3) which take part in hemocyte differentiation within the total bone marrow cells (FIGS. 5A and 5C) and within the c-Kit(+) Sca-1(+) fractions thereof (FIGS. 5B and 5D).

Graft-versus-host reaction (sometimes abbreviated below as "GVH reaction") refers herein to the reaction that arises when transplanted hematopoietic cells from the donor, owing to the immune response by the cells, attack recipient organs. The GVH reaction is provoked by the infiltration of donor T cells in, for example, the skin, liver or intestinal tract, and is characterized by causing, as the main symptoms, skin rashes, jaundice and/or diarrhea. The present invention is based on the discovery that delayed immune reconstitution or lowered immune function in a patient who has received a bone marrow transplant is caused by the GVH reaction to bone marrow (referred to below as the "bone marrow GVH reaction" or "bone marrow GVHD"). This mechanism is shown in FIG. 1. Following allogeneic hematopoietic stem cell transplantation, the transfused donor hematopoietic stem cells colonize blood marrow hematopoietic niches present in blood marrow microenvironments and proliferate, producing various leukocyte subsets or precursor cells. The mechanisms of blood marrow GVHD are thought to be the indirect suppression of hematopoiesis via impairment of bone marrow hematopoietic niches by donor T cells and the direct suppression of hematopoiesis in which inflammatory factors such as IFN and TNF suppress hemocyte proliferation and differentiation. As shown in the examples, the Fas-FasL pathway participates to some degree in bone marrow GVHD via donor T cells; moreover the donor T-cell subset which is the main cause of bone marrow GVHD is $CD4^+$ cells. Such bone marrow GVHD stops the production and differentiation of B cells in the recipient and at the same time also suppresses the production of granulocytic cells and T cells, thus playing a large role in delayed immune reconstitution and increasing the opportunities for post-transplantation infection.

The "graft-versus-tumor effect" refers to the cancer or tumor growth suppressing, shrinking and eliminating effects that can be observed as a result of T cells present in the transplanted donor-derived hematopoietic stem cells recognizing and attacking the patient's cancer or tumor cells as foreign matter. This is therefore an effect which can be observed only in allogeneic transplantation involving the transfusion of cells collected from a donor having a different HLA type. This effect, with respect to leukemia in particular, is called the graft-versus-leukemia effect (GVL effect). Similarly, this effect is called the graft-versus-lymphoma effect with respect to lymphoma, and the graft-versus-myeloma effect with respect to multiple myeloma.

In the use of the drug of the present invention, the tumor patient who has received an allogeneic hematopoietic stem cell transplantation refers primarily to malignant tumor patients, examples of which include patients having one or more of the following carcinomas: hematopoietic system tumors, cancer of the large intestine, kidney cancer (e.g., clear cell carcinoma), melanoma (e.g., metastatic malignant melanoma), prostate cancer (e.g., hormone-refractory prostate adenocarcinoma), breast cancer, colon cancer, lung cancer (e.g., non-small-cell lung cancer), bone cancer, pancreatic cancer, skin cancer, head and neck cancer, skin or orbital malignant melanoma, ovarian cancer, rectal cancer, anal cancer, stomach cancer, testicular cancer, uterine cancer, fallopian tube carcinoma, endometrial carcinoma, cervical carcinoma, vaginal carcinoma, vulvar carcinoma, esophageal cancer, cancer of the small intestine, endocrine system cancer, thyroid cancer, parathyroid cancer, adrenal cancer, soft tissue sarcoma, urethral cancer, cancer of the penis, pediatric solid cancer, bladder cancer, kidney or ureteral cancer, renal pelvic carcinoma, tumors of the central nervous system (CNS), primary CNS lymphoma, tumor angiogenesis, vertebral tumors, brain stem glioma, pituitary adenoma, Kaposi sarcoma, epidermoid cancer, squamous cell cancer, and environmentally induced cancers, including asbestos-induced cancers. Here, tumor patients in whom the use of the drug of the present invention is preferred are hematopoietic system tumor patients.

Hematopoietic system tumors are exemplified by leukemia and malignant lymphoma. Examples of leukemia include lymphatic leukemia (e.g., hairy cell leukemia, acute lymphatic leukemia, prolymphocytic leukemia, chronic lymphatic leukemia (e.g., B-cell chronic lymphatic leukemia), adult T-cell leukemia (adult T-cell lymphoma, adult T-cell leukemia bone marrow infiltration), lymphatic leukemia bone marrow infiltration), myeloma (e.g., plasma cell leukemia, solitary myeloma, multiple myeloma (e.g., Bence Jones multiple myeloma, multiple myelomatous joint disease, non-secretory multiple myeloma, myeloma kidney, multiple myeloma bone marrow infiltration), myelodysplastic syndrome (e.g., RAEB, RAEB-t, refractory anemia, RARS (primary sideroblastic anemia)), myeloid leukemia (e.g., acute myeloid leukemia, acute myelomonocytic leukemia, acute promyelocytic leukemia, basophilic leukemia, eosinophilic leukemia, neutrophilic leukemia, myelomonocytic leukemia, chronic myeloid leukemia (e.g., malignant changes in chronic myeloid leukemia, chronic phase of chronic myeloid leukemia, transitional stage of chronic myeloid leukemia, atypical chronic myeloid leukemia), chronic myelomonocytic leukemia (e.g., juvenile myelomonocytic leukemia), myeloid leukemia bone marrow infiltration), acute leukemia, chronic leukemia, monocytic leukemia (e.g., acute monocytic leukemia, chronic monocytic leukemia), smoldering leukemia, Letterer-Siwe disease, acute histiocytosis, acute mastocytoma, acute megakaryoblastic leukemia, plasmacytoma, myelofibrosis (e.g., acute myelofibrosis, primary myelofibrosis, secondary myelofibrosis, idiopathic myelofibrosis), myeloproliferative diseases, mixed cell leukemia, meningeal leukemia, erythroid leukemia, monoclonal immunoglobulinemia, hypoplastic leukemia, secondary leukemia, leukemic joint disease, atypical leukemia, mast cell leukemia, mast cell tumor disorders, and Crow-Fukase syndrome. Examples of malignant lymphoma include B cell lymphoma, diffuse lymphoma (e.g., diffuse mixed lymphoma, diffuse small cell lymphoma, diffuse small cleaved cell lymphoma, diffuse large cell lymphoma, diffuse undifferentiated lymphoma, lymphoblastocytic lymphoma, immunoblastocytic lymphadenopathy, reticulosarcoma), Hodgkin's disease (e.g., lymphocyte depleted Hodgkin's disease, lymphocyte predominant Hodgkin's disease, nodular sclerosing Hodgkin's disease, mixed cell Hodgkin's disease), lymphoma, malignant lymphoma of the stomach, orbital malignant lymphoma, malignant lymphoma of the neck, malignant lymphoma of the thyroid gland, malignant lymphoma of the bones, malignant lymphoma of the duodenum, malignant mediastinal lymphoma, malignant lymphoma of the small intestine, malignant lymphoma of the large intestine, malignant lymphoma of the brain, non-Hodgkin's lymphoma, peripheral T-cell lymphoma (e.g., T zone lymphoma, Sézary syndrome, Lennert lymphoma, mycosis fungoides), malignant tonsillar lymphoma, malignant lymphoma of the spleen, follicular cell lymphoma (e.g., medium-sized cell type follicular cell lymphoma, mixed cell type follicular cell lymphoma, large cell type follicular cell lymphoma), MALT lymphoma, malignant lymphoma of the heart, malignant lymphoma of the colon, malignant lymphoma of the rectum, malignant lymphoma bone marrow infiltration, malignant immunoproliferative diseases (e.g., alpha-H chain disease, gamma-H chain disease, primary macroglobulinemia, immunoproliferative small intestinal disease), and malignant lymphoma of the nose and throat. Here, hematopoietic system tumors in which the use of the drug of the present invention is preferred are acute leukemias.

"Allogeneic hematopoietic stem cell transplantation" in the use of the drug of the present invention refers herein to a method of reconstituting hematopoiesis by transfusing hematopoietic stem cells from a related donor or an unrelated donor having an HLA type that is identical or similar. In order to collect or acquire the hematopoietic stem cells, it is necessary first to screen the HLA types of relatives or to search bone marrow banks (e.g., the Japan Marrow Donor Program) or umbilical cord blood banks (e.g., the Japanese Cord Blood Bank Network) for a donor having a HLA type which is identical or similar to that of the patient. Allogeneic hematopoietic stem cell transplantation can be expected to have a GVT effect, but there is a risk of GVHD onset. It is for this reason that the drug of the present invention is effective. Another type of hematopoietic stem cell transplantation is autologous hematopoietic stem cell transplantation which is a method of reconstituting hematopoiesis by transfusing one's own hematopoietic stem cells. However, the need for the drug of the present invention is low in such cases because there is no concern over GVHD and there is little GVT effect.

Hematopoietic stem cell transplantation falls into three categories, depending on the type of cell used in transplantation: bone marrow transplantation, peripheral blood stem cell transplantation and umbilical cord blood transplantation, each to which the drug of the present invention can apply. Bone marrow transplantation is a method of transplanting hematopoietic stem cells by transplanting bone marrow fluid. Bone marrow fluid can be obtained by placing the donor under general anesthesia and using a bone marrow needle to collect about 15 to 20 mL of fluid per body weight from three to five places on the left and right sides of the dorsum of the pelvis. Peripheral blood stem cell transplantation is a method wherein peripheral blood stem cells which have been mobilized in a large quantity from the bone marrow into the blood by G-CSF administration is transplanted. Peripheral blood stem cells can be obtained by subcutaneously injecting about 10 μg/kg/day of G-CSF for 4 to 6 days, and using a blood component collection system to collect the cells on days 4 to 6 following injection. The timing of cell collection can be set by measuring the number of cells positive for the CD34 antigen, which is a hematopoietic stem cell marker present in the blood. Umbilical cord blood transplantation is a method of transplanting hematopoietic stem cells present in umbilical cord blood. Cord blood which matches the patient can be sought from a cord blood bank by means of a HLA type test. In cord blood transplantation, although the number of stem cells that can be collected from umbilical cord blood is limited, compared with the other types of transplantation, GVHD does not readily arise. As a result, even if two out of six HLA type are incompatible, transplantation is possible. Each of the above methods of transplantation and methods of collecting, preparing or screening for bone marrow, peripheral blood stem cells or umbilical cord blood can be carried out based on Manual of hematopoietic stem cell transplantation and diagnosis, first edition (published by Nihon Igakukan), or Manual of hematopoietic cell transplantation, revised third edition (published by Nihon Igakukan).

The donor for the allogeneic hematopoietic stem cell transplantation may be selected based on the HLA (human leukocyte antigen) type. Given that three HLA types (HLA-A, -B and -DR) are inherited from each parent, in principle, the number of HLA types which should be considered in allogeneic hematopoietic stem cell transplantation is six. Because HLA type incompatibility can cause severe GVHD after transplantation, it is desirable for the HLA type to be matched. However, a certain degree of incompatibility may have the opposite effect of leading to a strengthened GVT effect. Hence, it is preferable to select a suitable donor according to the type of tumor, the age and health status of the patient, and the type of hematopoietic stem cell to be transplanted. Donor selection is carried out based on, in principle, the following classification.
(1) HLA-matched related donors. Because the HLA type is inherited, there is a ¼ probability of compatibility among siblings. For this reason, the frequency of GVHD and transfusion-related complications is generally low. In allogeneic hematopoietic cell transplantation, it is desirable first to seek a compatible donor from among relatives.
(2) HLA-matched unrelated donors. In cases where an HLA-matched relative for all the HLA types has not been found, an HLA-matched person (HLA-matched unrelated donor) can be sought from a bone marrow bank.
(3) HLA-mismatched related donors. Given that the success rate for allogeneic hematopoietic stem cell transplantation from related donors in which five of the six HLA types match is comparable to that from HLA-matched non-related donors, even in cases where a relative that matches for all HLA types has not been found, a related donor with a partial mismatch may be selected.
(4) HLA-mismatched unrelated donors. In cases where a suitable donor cannot be found from among HLA-matched individuals or HLA-mismatched relatives, an HLA-mismatched unrelated person may be selected as the donor. However, in such cases, there is an increased risk of GVHD.

In addition, in selecting the donor, it is preferable to make a judgment which is also based on, for example, respiratory function, circulatory function, liver function, medical history for various diseases, and the presence or absence of infections and allergies. For more detailed selection criteria, reference may be made to Manual of hematopoietic stem cell transplantation and diagnosis, first edition (published by Nihon Igakukan), or Manual of hematopoietic cell transplantation, revised third edition (published by Nihon Igakukan).

In connection with the use of the drug of the present invention, allogeneic hematopoietic stem cell transplantation includes also pre-transplant preparation. Here, "pre-transplant preparation" refers to treatment which is carried out prior to transplantation and involves anticancer drug administration, irradiation or a combination thereof, and also, where necessary, the administration of immunosuppressants, in order to eradicate cancer cells or lower the immunity of the patient so as to facilitate the engrafting of the donor's hematopoietic stem cells. Such pre-transplant preparation may be carried out from about 7 to 10 days prior to hematopoietic stem cell transplantation.

Examples of anticancer drugs which can be employed in pre-transplant treatment using the drug of the present invention include alkylating agents (e.g., cyclophosphamide, busulfan, melfalan, hydroxyurea, nimustine hydrochloride, carmustine, lomustine, ranimustine, nitramine, iphosphamide, melphalan thiotepa, carboquone, busulfan, dacarbazine, temozolomide, procarbazine hydrochloride, nitrogen mustard-N-oxide hydrochloride), antimetabolites (e.g., enocitabine, capecitabine, carmofur, cladribine, gemcitabine, cytarabine, cytarabine ocfosfate, methotrexate, mercaptopurine, fludarabine, fluorouracil, tegafur, tegafur uracil, tegafur-gimeracil-oteracil potassium, doxifluridine, nelarabine, hydroxycarbamide, pemetrexed, pentostatin, mercaptopurine), anticancer antibodies (e.g., daunorubicin hydrochloride, doxorubicin hydrochloride, pirarubicin, mitoxantrone, idarubicin hydrochloride, bleomycin, actinomysin D, aclarubicin, amrubicin, epirubicin, zinostatin stimalamer, peplomycin, mitomycin C, mitoxantrone), alkaloids (e.g., vincristine, vindesine, etoposide, irinotecan, etoposide, sobuzoxane, docetaxel, nogitecan, paclitaxel, vinorelbine, vinblastine), molecular markers (e.g., ibritumomab tiuxetan, imatinib, erlotinib, gefitinib, gemtuzumab ozogamicin, sunitinib, cetuximab, sorafenib, tamibarotene, trastuzumab, tretinoin, panitumumab, bevacizumab, bortezomib, rituximab), and platinum-containing drugs (e.g., oxaliplatin, carboplatin, cisplatin, nedaplatin). Anticancer drug administration protocols may be carried out according to commonly known methods in this field.

The irradiation which can be employed in pre-transplant treatment using the drug of the present invention may be carried out according to a commonly known protocol in this field. For example, it is preferable for irradiation to be carried out by total-body irradiation for acute leukemia, malignant lymphoma and some solid carcinomas, and by local irradiation for ordinary solid carcinomas. The dose required will vary depending on such factors as the method of irradiation (single-dose or fractionated exposure), the type of tumor, and the susceptibility of the tumor to radiation. For example, in total-body irradiation, 10 to 12 Gy is regarded as a standard dose. On the other hand, to reduce organ damage from radiation, frequent use is being made recently of fractionated irradiation. For example, irradiation may entail one or two exposures daily at a dose level of about 1.8 to 2 Gy per exposure for a period of about 4 to 7 days. The fractionated irradiation may be equally fractionated exposure or unequally fractionated exposure, and may be suitably modified according to the burden on the patient, side effects and the therapeutic effects. Radiation therapy may be carried out in parallel with anticancer drug therapy.

The types and dosages of anticancer drugs or the dose of radiation when using the drug of the present invention may be selected in accordance with the type of tumor or hematopoietic stem cell or in accordance with the age or health status of the patient. The drug of the present invention may be employed either in "allogeneic hematopoietic stem cell transplantation with a myeloablative pre-transplant regimen (myeloablative transplantation)" involving the use of a conventional powerful pre-transplant regimen, or in "allogeneic hematopoietic stem cell transplantation with a non-myeloablative pre-transplant regimen (non-myeloablative transplantation)" which is able to reduce the toxicity by weakening the strength of the pre-transplant regimen (see Manual of hematopoietic stem cell transplantation and diagnosis, first edition (published by Nihon Igakukan), or Manual of hematopoietic cell transplantation, revised third edition (published by Nihon Igakukan)).

In addition, an immunosuppressant (e.g., cyclosporine, tacrolimus) may be optionally administered to keep acute GVHD from occurring.

In the present invention, "$CD4^+$ cell-depleting substance" refers to, for example, a substance which eradicates donor-derived $CD4^+$ cells or a substance which suppresses the proliferation or function of donor-derived $CD4^+$ cells. Examples include CD4 antibodies having a complement-dependent cytotoxicity (abbreviated below as "CDC") and/or an antibody-dependent cytotoxicity (abbreviated below as "ADC"), or such CD4 antibodies to which a cytotoxin or a cytotoxic drug has been added.

Here, "$CD4^+$ cells" refers to immune cells which express CD4 at the cell surface. Examples include $CD4^+$ T cells, $CD4^+$ dendritic cells, $CD4^+$ macrophages and $CD4^+$ NKT cells. The contribution of $CD4^+$ T cells to the onset of bone marrow GVHD in the present invention is especially large.

Here, the CD4 antibodies may be any which bond to human CD4 and, by destroying $CD4^+$ cells or suppressing their proliferation or function, reduce or eliminate such cells from the patient's blood or various tissues. However, humanized anti-human CD4 antibodies and human anti-human CD4 antibodies are preferred.

Here, "humanized anti-human CD4 antibody" refers to an antibody obtained by grafting the complementarity determining region (also referred to as "CDR") of an anti-human CD4 antibody derived from another mammal such as a mouse onto the framework (also referred to as "FR") sequence of a human antibody. Such an antibody may be produced based on the methods described in, for example, U.S. Pat. Nos. 4,816,567, 5,225,539, 5,530,101, 5,585,089 and 6,180,370. Anti-human CD4 antibodies derived from other mammals may be produced by, for example, the hybridoma technique (Kohler, G. et al., Nature, 256(5517), 495-497 (1975)). Amino acids on the FR in the variable region of the antibody may be substituted so that the CDR of the humanized anti-human CD4 antibodies forms a suitable antigen-bonding site (Sato, K. et al., Cancer Research, 53, 851-856 (1993)).

"Human anti-human CD4 antibody" is an anti-human CD4 antibody in which the entire structure of the CDR and FR, etc. is derived from humans. Such antibodies may be produced using an HuMAb mouse (registered trademark) (see, for example, U.S. Pat. Nos. 5,545,806, 5,569,825, 5,625,126 and 5,633,425), a KM mouse (registered trademark) (see WO 02/43478), a XenoMouse (registered trademark) (see U.S. Pat. Nos. 5,939,598, 6,075,181, 6,114,598, 6,150,584 and 6,162,963), a TC mouse (registered trademark) (see Tomizuka et al., Proc. Natl. Acad. Sol. USA 97(2), 722-727 (2000), or a human immune cell-reconstituted SCID mouse (see U.S. Pat. Nos. 5,476,996 and 5,698,767). The human anti-human CD4 antibody may also be prepared by a phage display method for human immunoglobulin gene library screening (see U.S. Pat. Nos. 5,223,409, 5,403,484 and 5,571,698).

The CD4 antibody in the present invention also includes such antibody fragments as Fab, F(ab)'$_2$ and ScFv of the above antibody, and low-molecular antibodies such as Sc(Fv)$_2$ and diabodies.

Isotypes of the CD4 antibody include IgG (IgG$_1$, IgG$_2$, IgG$_3$ and IgG$_4$), IgA (IgA$_1$ and IgA$_2$), IgM, IgD and IgE. IgG is preferred, and IgG$_1$ or IgG$_3$, in which the ADCC or CDC is stronger, are even more preferred.

In addition, the latent immunogenicity of the CD4 antibody in the present invention can be lowered by changing at least one residue within the FR or at least one residue within at least one CDR and removing a T-cell epitope (see U.S. Patent Publication No. 20030153043).

Also, by altering or modifying the variable region or constant region of the CD4 antibody in the present invention, it is possible to change the antigen-binding activity, stability, biological half-life, complement-fixing activity, CDC, Fc receptor-binding activity and/or ADCC.

The antigen compatibility of the CD4 antibody in the present invention can be increased by eliminating the glycosylating site on the variable region FR via an amino acid substitution (see U.S. Pat. Nos. 5,714,350 and 6,350,861). Also, by altering the number of cysteine residues in the hinge region of CH1, the assembly of heavy chains and light chains can be promoted or the antibody stability can be enhanced (U.S. Pat. No. 5,677,425). In addition, the biological half-life can be lengthened by the amino acid substitutions mentioned in U.S. Pat. No. 6,277,375 or 5,869,046 and U.S. Pat. No. 6,121,022, or by PEG conversion using a method known in this technical field.

Moreover, with regard to the CD4 antibody in the present invention, the effector function can be altered by an amino acid substitution in the Fc region (see U.S. Pat. Nos. 5,624,821 and 5,648,260), the CDC can be enhanced by the method described in U.S. Pat. No. 6,194,551, and the complement-fixing activity can be enhanced by the method described in WO 94/29351.

Also, the affinity of the CD4 antibody in the present invention to ADCC and/or Fcγ receptors can be enhanced by the method described in WO 00/42072. Similarly, the antibody ADCC can be increased by using the methods or cells described in U.S. Patent Publication No. 20040110704, EP Patent No. 1,176,195, WO 03/035835 or WO 99/54342 to alter glycosylation or reduce the fucose residues.

Here, preferred examples of the CD4 antibody in the present invention include MTRX-1011A, TRX-1 (see WO 2002/102853), Ibalizumab (see WO 92/09305), BT-061, huB-F5 and Zanolimumab (see WO 97/13852), 4162W94, Clenoliximab or Keliximab (see WO 93/02108), AD-519 or PRO-542 (see WO 92/13947), and Cedelizumab (see WO 96/36359).

To increase the $CD4^+$ cell-depleting ability, the CD4 antibody in the present invention may optionally bind a cytotoxic molecule such as a cytotoxin or a cytotoxic drug. Illustrative examples of cytotoxins include taxol, cytochalasin B, gramicidin D, ethidium bromide, emetine, mitomycin, etoposide, teniposide, vincristine, vinbastine, colchicine, doxorubicin, daunorubicin, dihydroxyanthracenedione, mitoxantrone, mitramycin, actinomycin D, 1-dehydrotestosterone, glucocorticoid, procaine, tetracaine, lidocaine, propranolol, puromycin, duocarmycin, calicheamicin, maytansine, auristatin, and derivatives thereof. More preferred examples include duocarmycin, calicheamicin, maytansine, auristatin, and derivatives thereof. Meanwhile, illustrative examples of cytotoxic drugs include antimetabolites (e.g., metotrexate, 6-mercaptopurine, 6-thioguanine, cytarabine, 5-fluorouracil dacarbazine), alkylating agents (e.g., mechlorethamine, thioepa chlorambucil, melfalan, carmustine (BSNU), lomustine (CCNU), cyclophosphamide, busulfan, dibromomannitol, streptozotocin, mitomycin C, cis-dichlorodiamineplatinum (II)), anthracyclines (e.g., daunorubicin and doxorubicin), antibiotics (e.g., dactinomycin, bleomycin, mithramycin, anthramycin (AMC)), and antimitotic agents (e.g., vincristine, vinblastine). The binding of cytotoxins or cytotoxic drugs to CD4 antibodies may be carried out by a known method in this technical field.

The drug of the present invention may be used for the prevention of post-transplant infection, such as pathogenic viral infection, pathogenic bacterial infection, pathogenic fungal infection and pathogenic parasitic infection. Here, illustrative examples of pathogenic viruses include HIV, hepatitis viruses (e.g., HCV, HBV, HAV), herpesviruses (e.g., VZV, HSV-1, HAV-6, HSV-II, CMV, Epstein-Barr virus), adenoviruses, influenzaviruses, flaviviruses, echoviruses, rhinoviruses, coxsackieviruses, coronaviruses, respiratory syncytial viruses, mumps viruses, rotaviruses, measles viruses, rubella viruses, parvoviruses, vaccinia viruses, adult T-cell leukemia viruses (HTLV), dengue viruses, papillomaviruses, the molluscum contagiosum virus, polioviruses, rabies viruses, JC viruses, arboviruses, and encephalitis viruses. Illustrative examples of pathogenic bacteria include *chlamydia*, *rickettsia* bacteria, mycobacteria, pneumococci, staphylococci, streptococci, pneumococci, meningococci, gonococci, *Escherichia coli*, enterococci, conococcus, *Klebsiella*, *Proteus*, *Serratia*, *Pseudomonas*, *Legionella*, *Diphtheria*, *Salmonella*, and the bacteria responsible for cholera, tetanus, botulism, anthrax, plague, leptospirosis and Lyme disease. Illustrative examples of pathogenic fungi include *Candida* (e.g., *albicans*, *krusei*, *glabrata*, *tropicalis*), *Cryptococcus neoformans*, *Aspergillus* (e.g., *fumigatus*, *niger*), *Mucorales* (e.g., *Mucor*, *Absidia*, *Rhizopus*), *Sporothrix schenckii*, *Blastomyces dermatitidis*, *Paracoccidioides brasiliensis*, *Coccidioides immitis*, and *Histoplasma capsulatum*. Illustrative examples of pathogenic parasites include *Entamoeba hisolytica*, *Balantidium coli*, *Naegleria fowleri*, *Acanthamoeba* spp., *Giardia lamblia*, *Cryptosporidium* spp., *Pneumocystis carinii*, *Plasmodium vivax*, *Babesia microti*, *Trypanosoma brucei*, *Trypanosoma cruzi*, *Leishmania donovani*, *Toxoplasma gondii*, and *Ancylostoma braziliense*.

In the present invention, the CD4$^+$ cell-depleting substance as an active ingredient may be administered by a parenteral pathway, such as intravenously, intramuscularly, intracutaneously, peritoneally, subcutaneously or spinally, as an injection or infusion of a composition prepared, together with a pharmaceutically acceptable carrier.

The dose of CD4$^+$ cell-depleting substance is typically, for example, from about 0.1 to about 100 mg/kg, preferably from about 0.1 to about 50 mg/kg, and more preferably from about 1 to about 30 mg/kg.

The period of administration for the inventive drug is the same day as allogeneic hematopoietic stem cell transplantation or from 1 to about 60 days following transplantation, preferably from 1 to about 30 days after transplantation, more preferably from day 5 to day 14 after transplantation, and still more preferably from day 5 to day 7 after transplantation. In cases where myelosuppression associated with chronic GVHD is observed, additional administration may be carried out even more than 60 days after transplantation.

The inventive drug may be administered anywhere from once daily to once in about 60 days, although administration is preferably once daily, more preferably once in 3 days, and even more preferably once in 10 days.

The injection or infusion containing the CD4$^+$ cell-depleting substance in the present invention may be used as a solution, a suspension or an emulsion. The solution may use, for example, distilled water for injection, physiological saline, a glucose solution and an isotonic solution (e.g., a solution of sodium chloride, potassium chloride, glycerol, mannitol, sorbitol, boric acid, sodium borate, propylene glycol). In addition, the injection may also include, for example, stabilizers, solubilizing agents, suspending agents, emulsifying agents, soothing agents, buffers, preservatives, antiseptics and pH adjustors. Examples of stabilizers that may be used include albumin, globulin, gelatin, mannitol, glucose, dextran, ethylene glycol, propylene glycol, diethylene sulfite, ascorbic acid, sodium bisulfite, sodium thiosulfate, sodium edetate, sodium citrate and dibutylhydroxytoluene. Examples of solubilizing agents that may be used include alcohols (e.g., ethanol), polyalcohols (e.g., propylene glycol, polyethylene glycol), and nonionic surfactants (e.g., Polysorbate 80 (registered trademark), HCO-50). Examples of suspending agents that may be used include glycerol monostearate, aluminum monostearate, methylcellulose, carboxymethylcellulose, hydroxymethylcellulose and sodium lauryl sulfate. Examples of emulsifying agents that may be used include gum arabic, sodium alginate and gum tragacanth. Examples of soothing agents that may be used include benzyl alcohol, chlorobutanol and sorbitol. Examples of buffers that may be used include phosphoric acid buffers, acetic acid buffers, boric acid buffers, carbonic acid buffers, citric acid buffers, Tris buffers, glutamic acid buffers and ε-aminocaproic acid buffers. Examples of preservatives that may be used include methyl p-oxybenzoate, ethyl p-oxybenzoate, propyl p-oxybenzoate, butyl p-oxybenzoate, chlorobutanol, benzyl alcohol, benzalkonium chloride, sodium dehydroacetate, sodium edetate, boric acid and sodium borate. Examples of antiseptics that may be used include benzalkonium chloride, p-oxybenzoic acid and chlorobutanol. Examples of pH adjustors that may be used include hydrochloric acid, sodium hydroxide, phosphoric acid and acetic acid.

The injection or infusion may be produced by sterilization in the final step or by sterilization involving aseptic manipulation, such as filtration with a filter or the like, followed by filling into an aseptic container. Injections may be preserved by freezing or may be preserved after first removing water by freeze-drying. In the latter case, at the time of use, distilled water for injection or the like is added to the preserved injection so as to re-dissolved it for use.

The entire contents of all patents and reference documents explicitly cited in this specification are incorporated herein as part of this specification.

EXAMPLES

The present invention is described in detail below by way of examples, although the invention is not limited by these examples.

Example 1

Production of Animal Model of GVHD after Allogeneic Hematopoietic Stem Cell Transplantation On the day prior to hematopoietic stem cell transplantation, the recipient mice (6-week-old female C57BL/6×DBA2 F1 (BDF1, H2$^{d/b}$)) were lethally irradiated (11 Gy) in two split doses given 3 hours apart. Some of the irradiated mice received both C57BL/6 (B6, H2$^b$)-derived T cell-depleted bone marrow cells (5×10$^6$ cells) and splenic T-cells (5×10$^6$ cells negatively enriched against CD11b, B220, Ter119 and NK1.1). These mice are referred to below as the GVHD group. Others of the irradiated mice received only the C57BL/6 (B6, H2$^b$)-derived T cell-depleted bone marrow cells (5×10$^6$ cells). The latter are referred to below as the BMT group.

Example 2

Flow Cytometric Analysis of Donor Hematopoietic Stem Cell-Derived Bone Marrow Hematopoiesis after Transplantation Bone marrow, spleen and thymus were harvested from each animal in each group of mice prepared in Example 1, and the donor hematopoietic stem cell-derived bone marrow hematopoiesis from day 7 to day 28 following transplantation was analyzed over time by flow cytometry. Flow cytometry was carried out by a method known to persons of ordinary skill in the art.

FIGS. 2(A) to (I) show the change over time in the number of each of the following cells in BMT and GVHD groups: total bone marrow cells, total splenic cells and total thymic cells; and in the number of each of the following cells in bone marrow within the BMT and GVHD groups: granulocytes, monocytes, erythroblastic cells (CD71$^+$ and Ter119$^{+/-}$), and splenic CD4$^+$ and CD8$^+$ T cells. Decreases in the total number of bone marrow, splenic and thymic cells in the GVHD group, a recovery in splenic CD4$^+$ T-cells in the BMT group, and a decrease in erythroblastic cells in the GVHD group were observed.

Example 3

Production of Animal Model of GVHD after Allogeneic Hematopoietic Stem Cell Transplantation (2)

On the day prior to hematopoietic stem cell transplantation, CD45.2$^+$ recipient mice (6-week-old female C57BL/6 ×DBA2 F1 (BDF1, H2$^{d/b}$)) were lethally irradiated (11 Gy) in two split doses given 3 hours apart. Some of the irradiated mice received both CD45.1$^+$CD45.2$^+$ congenic mouse-derived T cell-depleted bone marrow cells (5×10$^6$ cells) and CD45.1$^+$ congenic mouse-derived splenic T-cells (5×10$^6$ cells negatively enriched against CD11b, B220, Ter119 and NK1.1). These mice are referred to below as the GVHD group. Others of the irradiated mice received only the CD45.1$^+$CD45.2$^+$ congenic mouse-derived T cell-depleted bone marrow cells (5×10$^6$ cells). The latter are referred to below as the BMT group.

Example 4

Flow Cytometric Analysis of Donor Hematopoietic Stem Cell-Derived Bone Marrow Hematopoiesis after Transplantation (2)

Bone marrow, spleen and thymus were harvested from each animal in the groups of mice prepared in Example 3, and the donor hematopoietic stem cell-derived bone marrow hematopoiesis from day 7 to day 28 following transplantation was analyzed over time by flow cytometry. Flow cytometry was carried out by a method known to persons of ordinary skill in the art.

FIGS. 3(A) to (F) show the change over time in the number of each type of donor T cell and donor bone marrow-derived cell in the BMT and GVHD groups. Recovery by the donor bone marrow-derived T-cells is delayed in the GVHD group compared with the BMT group. Moreover, although the donor bone marrow-derived T-cells in the GVHD group is suppressed, they are gradually producing.

FIGS. 4(A) to (D) show the change over time in the number of B cells in the bone marrow and the thymus in the BMT and GVHD groups. In the GVHD group, excessive impairment of B-cell differentiation and production persists throughout.

Hence, in the GVHD group, declines in the myelocytic and erythroblastic cells, and in particular a delayed recovery of systemic T-cells and B-cells due to delayed recovery of lymphatic progenitor cells, are observed. These results indicate that immunosuppression by GVHD has occurred.

Example 5

Analysis of Hemocyte Differentiation by Real-Time RT-PCR

To determine which stage of hemocyte differentiation the bone marrow GVHD impairs, bone marrow was harvested from the GVHD murine models produced in Example 1, the total RNA was prepared by a method known to persons of ordinary skill in the art, and the mRNA expression of factors which participate in hemocyte differentiation (CXCL12, Pax5, E2a, Ebf1, IFNgamma, IL-7R, Irf1, GATA3) was analyzed by real-time RT-PCR. The real-time RT-PCR was conducted by a method known to persons of ordinary skill in the art.

FIGS. 5(A) to (D) shows the results obtained by concentrating and analyzing the total bone marrow cells and the c-Kit(+)Sca-1(+) fraction thereof. In the GVHD group, extreme declines are apparent in the expression of Pax5, E2a and Ebf1, which are transcription factors essential for B-cell differentiation and proliferation. A decrease in IL-7R, which is required for the differentiation of lymphocyte precursors, was also observed. These results indicate that, due to the onset of GVHD, the production and differentiation of B-cells is specifically or continuously impaired from a very early stage.

Example 6

Immunohistological Staining of Intestinal Tract and ELISA Analysis of Fecal IgA

To understand the influence of GVHD on intestinal tract Immunity, the intestinal tracts and feces of the GVHD murine models prepared in Example 1 were collected, and immunohistological staining of the intestinal tract and ELISA measurement of fecal IgA were carried out. Immunohistological staining and ELISA analysis were carried out by methods known to persons of ordinary skill in the art.

Figure 6:
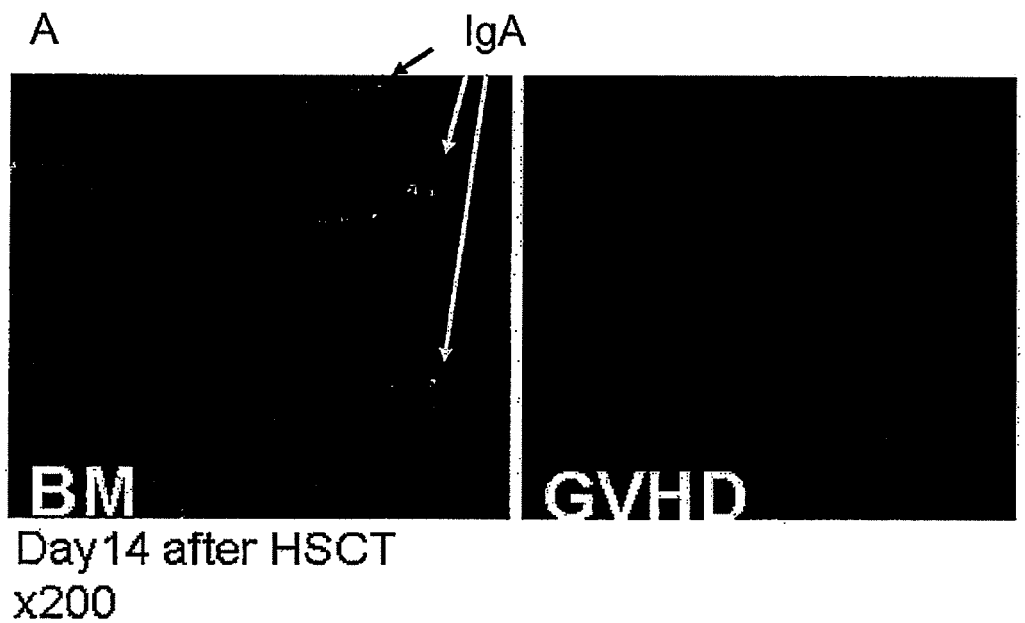
FIG. 6 shows immunohistological staining patterns (×200) in the intestinal tract and fecal IgA concentrations (using ELISA) on day 14 after transplantation in the BMT and GVHD groups.
Figure 6:
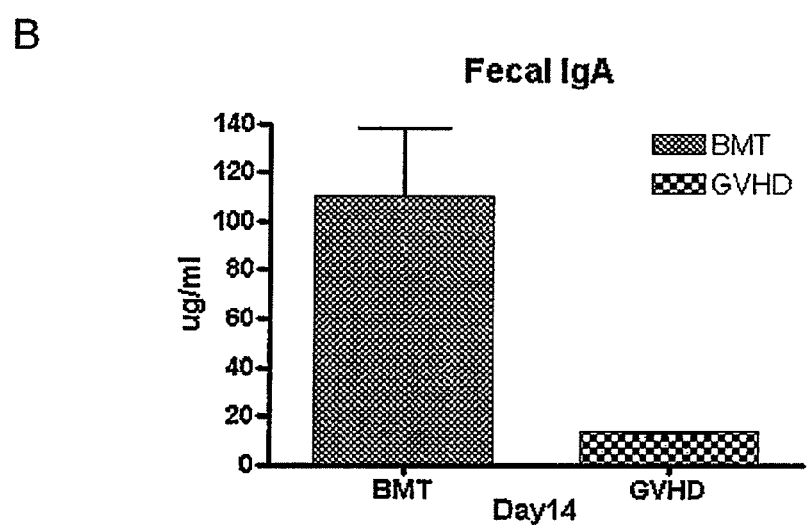

FIGS. 6(A) and (B) shows intestinal tract immunohistological staining patterns (×200) and fecal IgA concentrations on day 14 after transplantation in the BMT and GVHD groups, respectively. IgA production was clearly depressed (disappearance of light areas indicated by arrows in immunohistological staining patterns) in the GVHD group compared with the BMT group. The same was also true of the ELISA measurements of fecal IgA. These results show that IgA production is impaired in GVHD.

Example 7

Pathological Analysis in Bone Marrow at Time of GVHD Onset

Bone marrow sections on day 21 after transplantation were prepared for the GVHD murine models produced in Example 1, and hematoxylin-eosin staining was carried out. Hematoxylin-eosin staining was carried out by a method known to persons of ordinary skill in the art.

Figure 7:
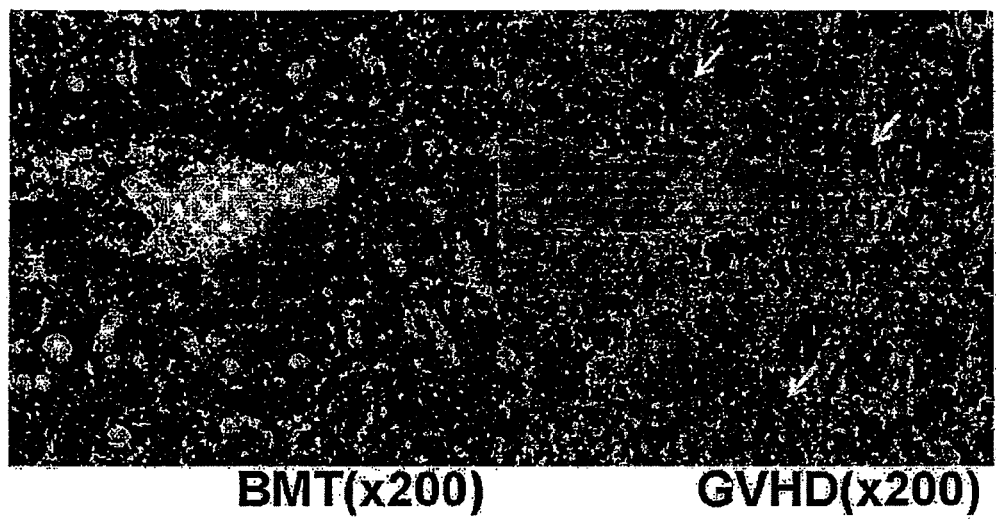
FIG. 7 shows hematoxylin-eosin stained images of bone marrow sections on day 21 after transplantation in murine models of GVHD.

As shown in FIG. 7, a distinct decline in the number of nucleated cells (the number of cells represented on the image by black shadows) and spotted clusters of erythrocytes (arrows) in the GVHD group were observed. These were characteristic bone marrow findings associated with GVHD. Although not shown, in the GVHD group on day 28 after transplantation, bleeding and blood clots within the bone marrow were conspicuous, indicating severe breakdown of the normal structure.

At the same time, although not shown, the distinct decline in cellularity and the hemorrhagic picture observed in the GVHD group on day 21 after transplantation improved in the group given CD4 antibodies. Specifically, a recovery in the number of nucleated bone marrow was observed and the spotted clusters of erythrocytes decreased. It should be noted that 200 μg of the CD4 antibodies (GK1.5, Medical & Biological Laboratories) was administered intraperitoneally once each on days 4 and 6 after transplantation in the above GVHD murine models.

Example 8

Analysis of GVHD Sites of Action in Bone Marrow Tissue

To identify the GVHD sites of action in the bone marrow tissue, bone marrow was harvested from the GVHD murine models produced in Example 1, total RNA was prepared by a method known to persons of ordinary skill in the art, and the expression of SAF-1 (CSCL12) was measured over time by real-time RT-PCR. SDF-1 is one hematopoiesis-associated molecule which is essential during interactions with bone marrow stroma at sites of proliferation and differentiation by hematopoietic stem cells and hemocytic precursor cells at various stages of differentiation. Real-time RT-PCR was carried out by a method known to persons of ordinary skill in the art.

Figure 8:
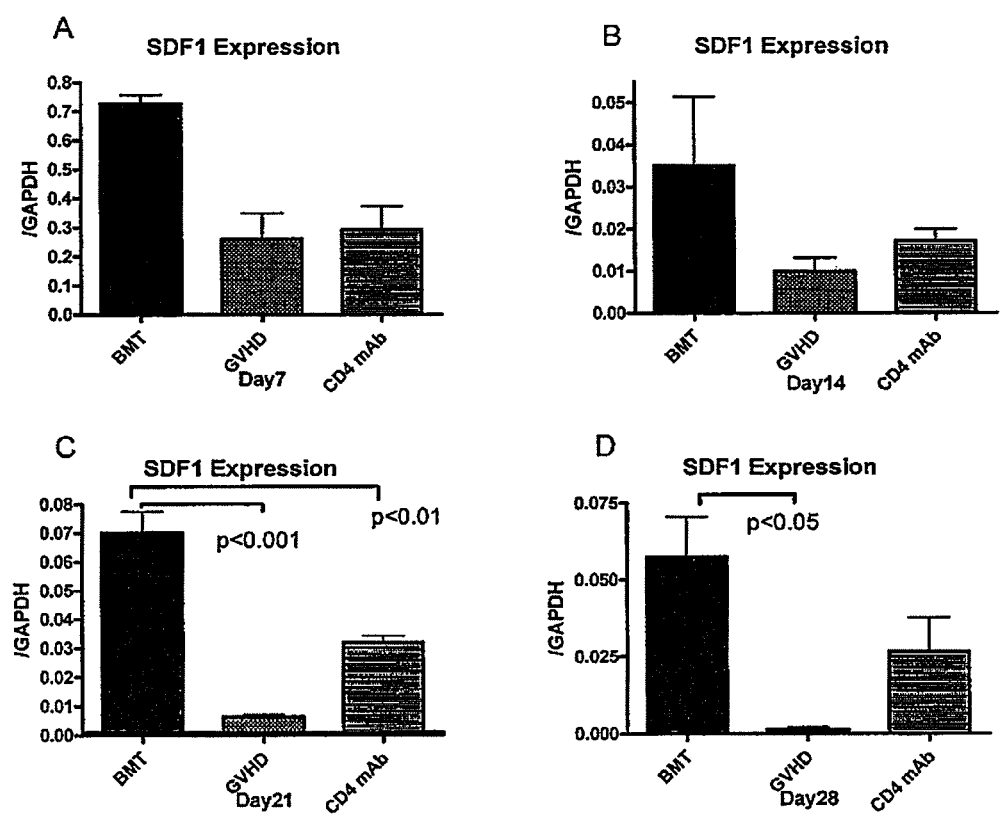
FIG. 8 shows SDF-1 (CXCL12) expression in the bone marrow within the BMT and GVHD groups.

As shown in FIGS. 8(A) to (D), the expression decreased markedly in the GVHD group. This result indicates that the bone marrow stroma is a target for GVHD. This is also supported by the absence of a significant difference between the GVHD group and the BMT group in the expression of SDF-1 receptor CXCR4 on B cells and is moreover corroborated by the fact that, even in transplantation experiments using mutant Fas-containing lpr mouse-derived bone marrow cells, B cell production was unable to recover in the GVHD group. By contrast, in the group given CD4 antibodies, the decrease in SDF-1 expression showed an improving trend with the passage of time (FIGS. 8C and 8D).

Example 9

Identification of Effector Molecules which Induce Bone Marrow GVHD

On the day prior to hematopoietic stem cell transplantation, the recipient mice (6-week-old female C57BL/6 ×DBA2 F1 (BDF1, $H2^{d/b}$)) were lethally irradiated (11 Gy) in two split doses given 3 hours apart. The irradiated mice received as the transplanted bone marrow either C57BL/6 (B6, $H2^b$)-derived T cell-depleted bone marrow cells ($5\times10^6$ cells) or mutant Fas-containing lpr mouse-derived T cell-depleted bone marrow cells ($5\times10^6$ cells). In cases where GVHD was to be induced, the mice received ordinary wild-type (also referred to as WT) B6 splenic T cells ($5\times10^6$ cells negatively enriched against CD11b, B220, Ter119 and NK1.1) or mutant FasL-containing gld mouse-derived splenic T cells ($5\times10^6$ cells negatively enriched against CD11b, B220, Ter119 and NK1.1) in various combinations (also referred to as GVHD groups). The mutant FasL-containing gld mice and the mutant Fas-containing lpr mice were obtained from Japan SLC, Inc.

Figure 9:
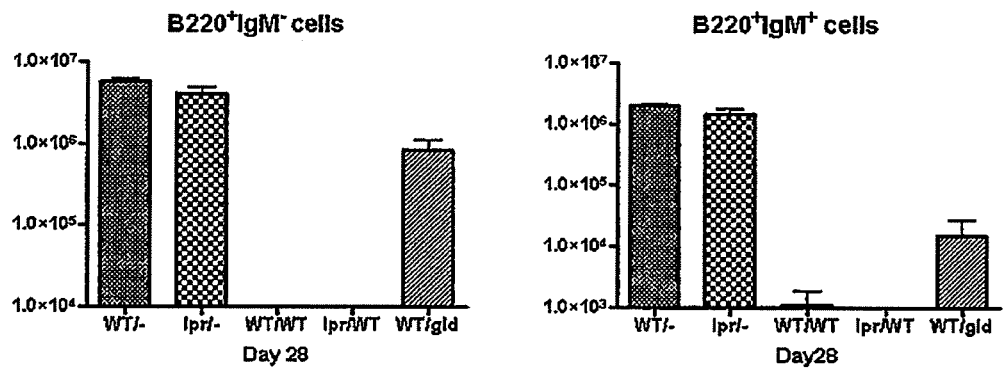
FIG. 9 shows B cell production and body weight change over time in experiments wherein mutant FasL-bearing gld mouse-derived splenic T cells and mutant Fas-bearing lpr mouse-derived bone marrow cells were used in various combinations (in the figures, combinations are labeled as "bone marrow cells/splenic cells" [BM/SPL]).
Figure 9:
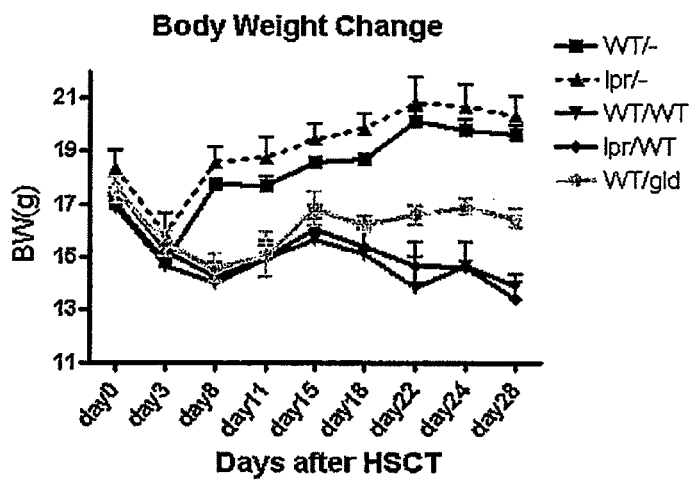

In FIG. 9, (WT/−), (lpr/−), (WT/WT), (lpr/WT) and (WT/gld) indicate the combination of bone marrow cells and splenic cells (bone marrow/spleen) at the time of transplantation.

Bone marrow was harvested from each animal in the respective groups of mice, and hemocyte differentiation from day 7 to day 28 after transplantation was analyzed over time by flow cytometry. Flow cytometry was carried out by a method known to persons of ordinary skill in the art.

As shown in FIGS. 9(A) to (C), partial recovery of the B cells was observed in the WT/gld group. This result shows that the FasL of the donor T cells plays a limited role in the onset of bone marrow GVHD. Also, because the recovery of B cells is not observed in the lpr/WT group in which mutant Fas-containing lpr mouse-derived bone marrow cells were used as the transplanted bone marrow cells, there is a possibility that the target of FasL is stromal cells rather than hemocytic cells. Also, the fact that hematopoiesis does not recover even though bone marrow which does not express Fas was transfused suggests the possibility that, instead of the bone marrow cells being directly impaired by the Fas-FasL pathway of the donor T cells, the bone marrow stromal cells which are the hematopoietic micro-environments that directly interfere with the bone marrow cells and play the essential role of "fields" for differentiation of the bone marrow cells are impaired.

Example 10

Identification of T-Cell Subset which Induces Bone Marrow GVHD

The CD4 antibody (200 μg) or the CD8 antibody (53-6.7, Medical and Biological Laboratories) mentioned in Example 7 were intraperitoneally administered to the GVHD murine models produced in Example 1, once each on days 4 and day 6 after transplantation, and, using improvement in GVHD as the indicator, the causative T cell subset was identified.

Figure 10:
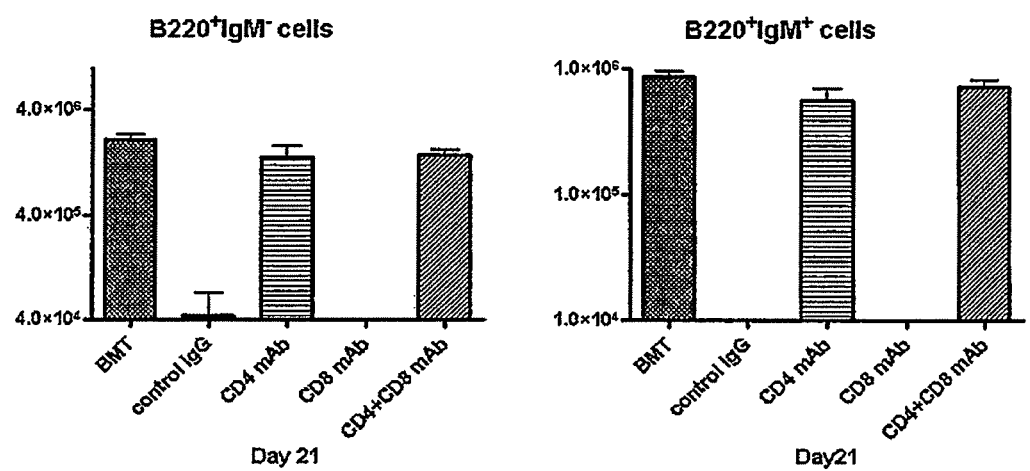
FIG. 10 shows the influence of administering CD4 antibody or CD8 antibody on the number of B cells.
Figure 11:
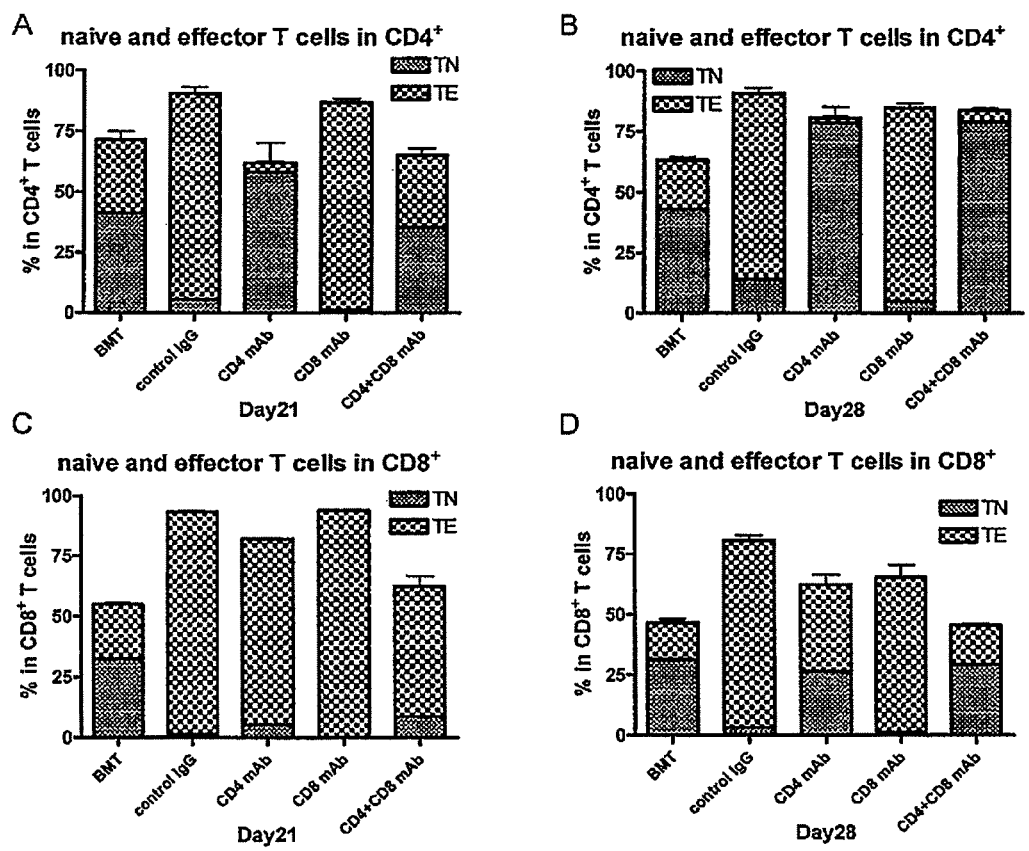
FIG. 11 shows the influence of administering CD4 antibody or CD8 antibody on the number of naive (TN) or effector (TE) $CD4^+$ T cells.
Figure 12:
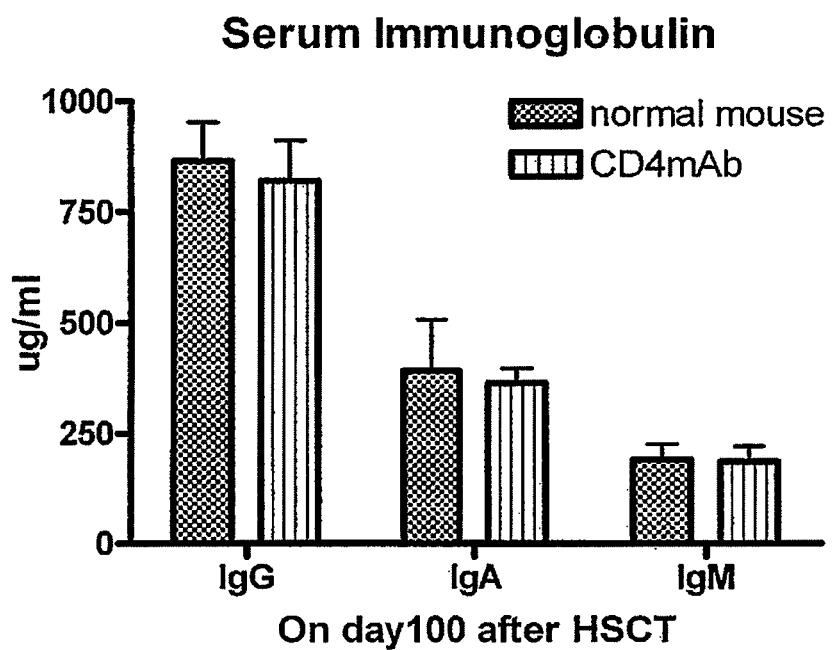
FIG. 12 shows the influence of CD4 antibody administration upon the serum immunoglobulin concentration on day 100 after transplantation.

As shown in FIG. 10, a marked recovery in B cells due to CD4 antibody administration can be observed, suggesting that CD4 is the main effector. On the other hand, no effects due to CD8 antibody administration were observed. An analysis of thymic T cell differentiation by flow cytometry demonstrated that, as shown in FIGS. 11(A) to (D), the recovery of naive T cells in the thymus was promoted by CD4 antibody administration. Also, as shown in FIG. 12, with the administration of CD4 antibody, a recovery in various types of immunoglobulins was observed on day 100 after transplantation.

Example 11

Action of CD4 Antibody on Bone Marrow GVHD and GVT Effect

To confirm the action of CD4 antibody administration on GVHD and on the GVT effect, the GVHD murine models produced in Example 1 were intravenously injected with $1\times10^4$ cells of P815 (a DBA2 mouse-derived mast cell tumor (ATCC: TIB-64)) 2 hours before bone marrow transplantation, and were intraperitoneally administered 200 µg of anti-CD4 antibody once each on days 4 and day 6 after transplantation. The survival of the mice, the GVHD scores and the changes in body weight were analyzed.

Figure 13:
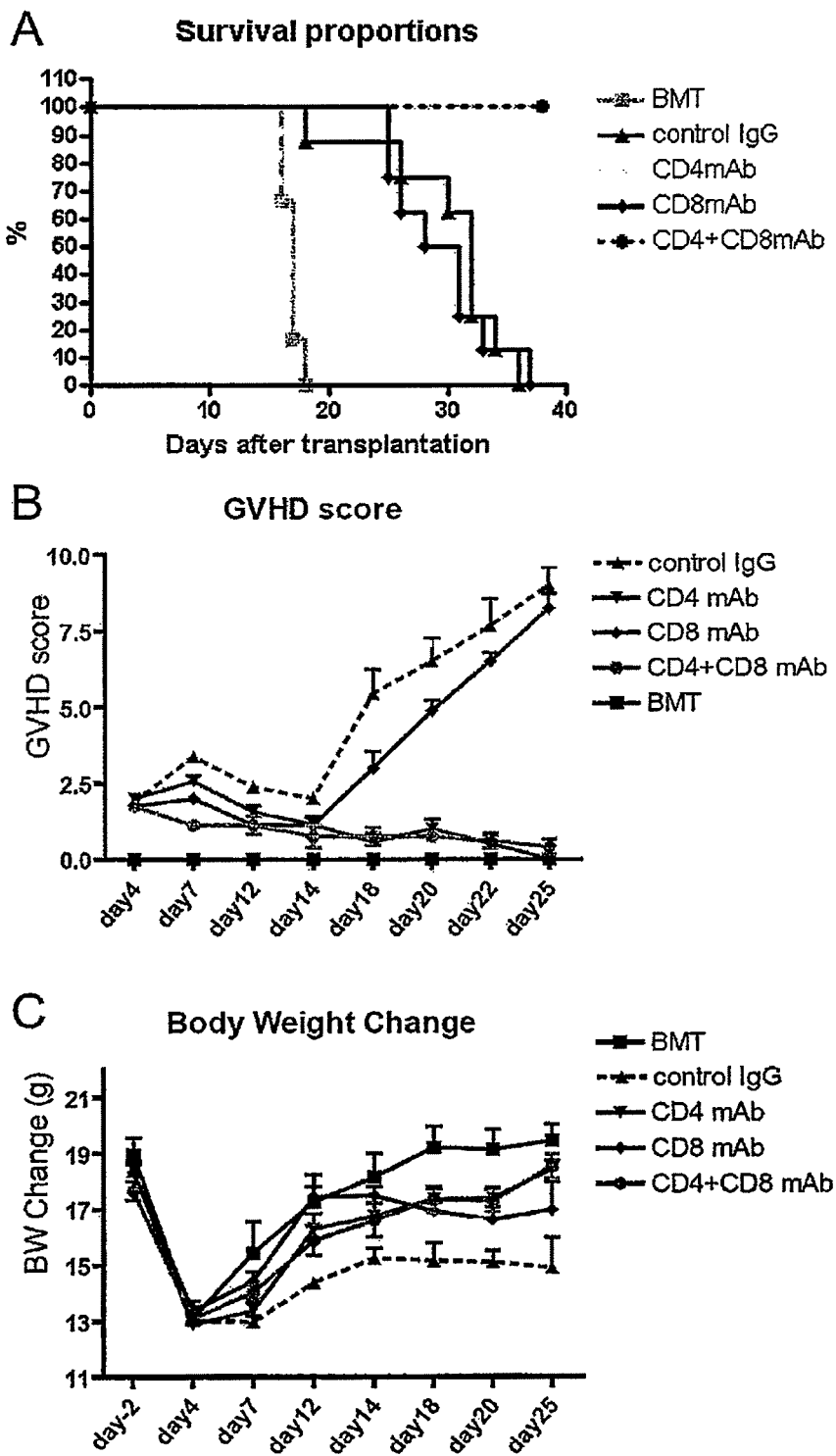
FIG. 13 shows the influence of CD4 antibody or CD8 antibody administration on the percent survival of murine models of GVDH (FIG. 13A: GVT effect with concurrent transfusion of P815 cells), the GVHD score (FIG. 13B), and the body weight change over time (FIG. 13C).

As shown in FIG. 13A to 13C, in the CD4 antibody group, the GVHD was suppressed without a loss in the GVT effect (13B), and 100% survival was maintained up to nearly day 40 following transplantation (13A). In the BMT group, tumor deaths due to the metastasis of tumor cells to the liver and spinal cord occurred on days 15 to 20 after transplantation.

Example 12

CD4 Antibody Therapy in Myeloablative Transplantation

Following various forms of chemotherapy (in the case of various types of acute or chronic leukemia, a single administration of a suitable amount of endoxan; in the case of malignant lymphoma, treatment involving any combination of suitable amounts of melfalan, endoxan, lastet and dexamethasone), total-body irradiation (TBI) at 12 Gy (fractionated exposure: 4 Gy per day for 3 days) is carried out from 1 to 3 days prior to transplantation, after which hematopoietic stem cell transplantation is carried out. Preferably, CD4 antibodies are administered once daily a total of three times from day 5 to day 7 after transplantation.

Example 13

CD4 Antibody Therapy in Non-Myeloablative Transplantation

Following chemotherapy (a combination of fludarabine and busulfan), TBI (2 to 4 Gy) is carried out as fractionated exposure for 1 to 2 days before transplantation, then hematopoietic stem cell transplantation is carried out. Next, CD4 antibodies are preferably administered once daily a total of three times from day 5 to day 7 after transplantation.

INDUSTRIAL APPLICABILITY

The present invention is useful in that it can prevent the risk of complications, particularly infections, associated with allogeneic hematopoietic stem cell transplantation.

The invention claimed is:

1. A prophylactic method of infection which maintains a graft-versus-tumor effect of allogeneic hematopoietic stem cell transplantation, wherein comprises administering an effective amount of a substance capable of depleting CD4 positive cells to a tumor patient who has received an allogeneic hematopoietic stem cell transplantation in the interval from day 1 to about day 60 following transplantation, from once a day to once in about 60 days.

2. The prophylactic method of infection according to claim 1, which comprises administering an effective amount of the substance capable of depleting CD4 positive cells in the interval from day 5 to day 14 following transplantation, from once a day to once in ten days.

3. The prophylactic method of infection according to claim 1, wherein the substance capable of depleting CD4 positive cells is a CD4 antibody or an altered and/or modified form thereof.

4. The prophylactic method of infection according to claim 3, wherein the CD4 antibody is a humanized anti-human CD4 antibody or a human anti-human CD4 antibody.

5. The prophylactic method of infection according to claim 3, wherein the CD4 antibody is administered in a dose of from 1 to 30 mg/kg each time.

6. The prophylactic method of infection according to claim 1, wherein the tumor is a hematopoietic tumor.

7. The prophylactic method of infections according to claim 6, wherein the hematopoietic tumor is acute leukemia, myeloma or malignant lymphoma.

8. The prophylactic method of infection according to claim 1, wherein the allogeneic hematopoietic stem cell transplantation is bone marrow transplantation, peripheral blood stem cell transplantation or umbilical cord blood transplantation.

9. The prophylactic method of infections according to claim 1, wherein a donor of the allogeneic hematopoietic stem cell transplantation is a HLA-matched related donor, HLA-matched non-related donor, HLA-mismatched related donor or HLA-mismatched non-related donor.

10. The prophylactic method of infection according to claim 1, wherein the allogeneic hematopoietic stem cell transplantation is non-myeloablative transplantation or myeloablative transplantation.

11. The prophylactic method of infection according to claim 1, wherein pre-transplant treatment in the allogeneic hematopoietic stem cell transplantation comprises anti-cancer drug administration, exposure to radiation, or a combination thereof.

12. The prophylactic method of infection according to claim 1, wherein the infection is pathogenic viral infection, pathogenic bacterial infection, pathogenic fungal infection or pathogenic parasitic infection.

13. The prophylactic method of infection according to claim 1, wherein the prophylaxis of infections comprises amelioration of delayed immune reconstitution due to a graft-versus-host reaction in bone marrow.

14. A promotional method of the immunological reconstitution which maintains a graft-versus-tumor effect of allogeneic hematopoietic stem cell transplantation, which comprises administering an effective amount of a substance capable of depleting CD4 positive cells to a tumor patient who has received an allogeneic hematopoietic stem cell transplantation in the interval from day 1 to about day 60 following transplantation, from once a day to once in about 60 days.

15. A prophylactic method of infection which maintains a graft-versus-tumor effect of allogeneic hematopoietic stem cell transplantation, comprising administering an effective amount of a humanized anti-human CD4 antibody to a tumor patient who has received an allogeneic hematopoietic stem cell transplantation in the interval from day 1 to about day 60 following transplantation, from once a day to once in about 60 days, and depleting donor CD4 positive T cells.

16. A prophylactic method of infection which maintains a graft-versus-tumor effect of allogeneic hematopoietic stem cell transplantation, comprising administering an effective amount of a substance capable of depleting CD4 positive cells to a tumor patient who has received an allogeneic hematopoietic stem cell transplantation in the interval from day 4 to about day 60 following transplantation, from once a day to once in about 60 days, and depleting donor CD4 positive T cells.

17. The prophylactic method of infection according to claim 16, wherein the substance capable of depleting CD4 positive cells is a humanized anti-human CD4 antibody.

* * * * *